(12) United States Patent
Mihaylov et al.

(10) Patent No.: US 9,574,975 B2
(45) Date of Patent: *Feb. 21, 2017

(54) DEVICE FOR FLUID SAMPLING

(71) Applicant: Nextteq LLC, Tampa, FL (US)

(72) Inventors: Gueorgui M. Mihaylov, Virginia Beach, VA (US); Bryan I. Truex, Tampa, FL (US)

(73) Assignee: NEXTTEQ LLC, Tampa, FL (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/184,198

(22) Filed: Feb. 19, 2014

(65) Prior Publication Data

US 2014/0318280 A1 Oct. 30, 2014

Related U.S. Application Data

(63) Continuation of application No. 13/028,587, filed on Feb. 16, 2011, now Pat. No. 8,714,035.

(60) Provisional application No. 61/305,011, filed on Feb. 16, 2010.

(51) Int. Cl.
*G01N 1/14* (2006.01)
*G01N 1/24* (2006.01)

(52) U.S. Cl.
CPC ............. *G01N 1/14* (2013.01); *G01N 1/24* (2013.01); *G01N 2001/1427* (2013.01)

(58) Field of Classification Search
CPC ..... G01N 1/14; G01N 1/24; G01N 2001/1427
USPC .................................................. 73/864.51
See application file for complete search history.

(56) References Cited

U.S. PATENT DOCUMENTS

| | | | | |
|---|---|---|---|---|
| 3,206,982 | A * | 9/1965 | Blondfield | G01N 1/2226 141/314 |
| 3,512,700 | A * | 5/1970 | Evans | B65D 31/00 383/120 |
| 5,437,384 | A | 8/1995 | Farrell | |
| 5,853,247 | A | 12/1998 | Shroyer | |
| 6,536,635 | B1 | 3/2003 | Garcia | |
| 6,550,967 | B2 * | 4/2003 | Hedaya | B65D 33/02 383/127 |
| 8,714,035 | B2 * | 5/2014 | Mihaylav | G01N 1/14 73/864.51 |
| 2008/0166819 | A1 | 7/2008 | Loomis et al. | |

FOREIGN PATENT DOCUMENTS

| | | | |
|---|---|---|---|
| GB | 2494721 | * | 3/2013 |
| JP | 490090275 | | 7/1949 |

(Continued)

OTHER PUBLICATIONS

Japanese Office Action and English Translation thereof ("Notice of Reasons for Rejection") issued by the Japanese Patent Office in corresponding Japanese Application No. 2012-553995 and mailed on Mar. 7, 2016.

*Primary Examiner* — J M Saint Surin
(74) *Attorney, Agent, or Firm* — Bernard G. Pike; Pike IP Law, PLLC (57) ABSTRACT

The disclosure is directed to a device for fluid sampling. The device may have two panels that are or may be adhered, attached or otherwise connected to opposite sides of a sampling bag having flexible walls. The panels may be used for conveniently inflating or deflating the sampling bag and obtaining fluid samples.

10 Claims, 10 Drawing Sheets

(56) References Cited

FOREIGN PATENT DOCUMENTS

| | | |
|---|---|---|
| JP | 510003283 | 1/1951 |
| JP | 510013670 | 2/1951 |
| JP | 530138332 | 10/1953 |
| JP | 460008395 | 3/1971 |
| JP | 52010191 A | 1/1977 |
| JP | 52018390 A | 2/1977 |
| JP | 55063736 A | 5/1980 |
| JP | 56073298 A | 6/1981 |
| JP | 620181391 | 11/1987 |
| JP | 070077484 | 3/1995 |

\* cited by examiner

DEVICE FOR FLUID SAMPLING

RELATED APPLICATIONS

This patent applications claims priority under 35 U.S.C. §120 to U.S. patent application Ser. No. 13/028,587 filed on Feb. 16, 2011 and under 35 U.S.C. §119 to U.S. Provisional Patent Application Ser. No. 61/305,001 filed on Feb. 16, 2010 which are both incorporated by reference in their entirety.

FIELD OF THE INVENTION

Embodiments of the present invention is directed to sampling of fluids and more particularly to air sampling with containers with flexible walls, referred to as sampling bags. Further, embodiments of the sampling bag may comprise panel attached to the exterior of the sampling bags. The panels may further comprise a handle configured to allow the sampling bags to be inflated and deflated by hand.

BACKGROUND OF THE INVENTION

Conventional containers for fluids may have rigid walls or flexible walls. Containers with rigid walls have a defined permanent volume for containing fluids and containers with flexible walls have variable or changeable volumes. Conventional containers include, but are not limited to, bottles, canisters and bags. Such containers may be used for a variety of purposes, including obtaining and holding fluid samples and containing standard gas mixtures that may be used for calibration of analytical instruments. As used herein, the term "fluid" includes gases and/or liquids. There are many configurations of such containers that have been developed and specialized for particular uses.

Gas mixtures under pressure are effective for preparing standard fluid mixtures in industrial quantities and preferably with comparably high concentration of one (or more) components in a carrier fluid. Gas mixtures under high pressure are typically stored in containers with rigid walls. For laboratory use, such gas mixtures may be diluted with additional carrier fluid to a desired concentration of a specific component in order to prepare a standard mixture. Conventional containers for transporting, preserving and use of such standard mixtures may be containers having flexible walls comprised of an inert, low-permeability material. Materials having low sorption on the walls for the components contained are preferred to increase the integrity of the mixture. Containers with flexible walls, also referred to as sampling bags, are widely used for fluid sampling, air sampling and liquid sampling. Materials such as Kynar and Tedlar are widely used for making such containers.

In order to obtain a representative sample or prepare an accurate standard, the containers must be properly prepared prior to filling. Typically, the bags are flushed with neutral gas and subjected to high vacuum to substantially remove all the fluid from the container with strong vacuum pumps. The bags should be purged and flushed to cause desorption of any residue and their volume should reduced to substantially zero. Any adsorbed residue or residual gas may contaminate any prepared fluid mixture or sample of fluid put in a poorly prepared bag.

Containers with rigid walls and flexible walls both have their own advantages and disadvantages. The disadvantages of containers with rigid walls include their extremely high price and expensive maintenance; they are bulky and, thus, their storage, transportation, and mailing costs are expensive; they have to be over pressurized when delivery of gas vapors or mixtures is needed; and completely vacuumed before used for fluid sampling.

Another drawback of sampling with containers with rigid walls is that after removing a portion of the sample from the container, the pressure in the canister may be reduced below atmospheric pressure and additional carrier gas (noble gas for example) may be added to increase the pressure back to atmospheric pressure. This process dilutes the sample or standard and analysis requires compensation for the additional carrier gas.

One method of filling container with rigid walls is to create a vacuum within the container. The driving force to get fluid into the container is provided by this vacuum. A small sampling pump cannot create a sufficient vacuum within the container; therefore, strong specialized vacuum pumps are needed.

An alternative to the containers with rigid walls are containers with flexible walls or bags. For containers with flexible walls, two methods of filling are known and widely used: (OSHA Technical Manual—Directive Number: 08-05 (TED 01), Effective Jun. 24, 2008)

Figure 8:
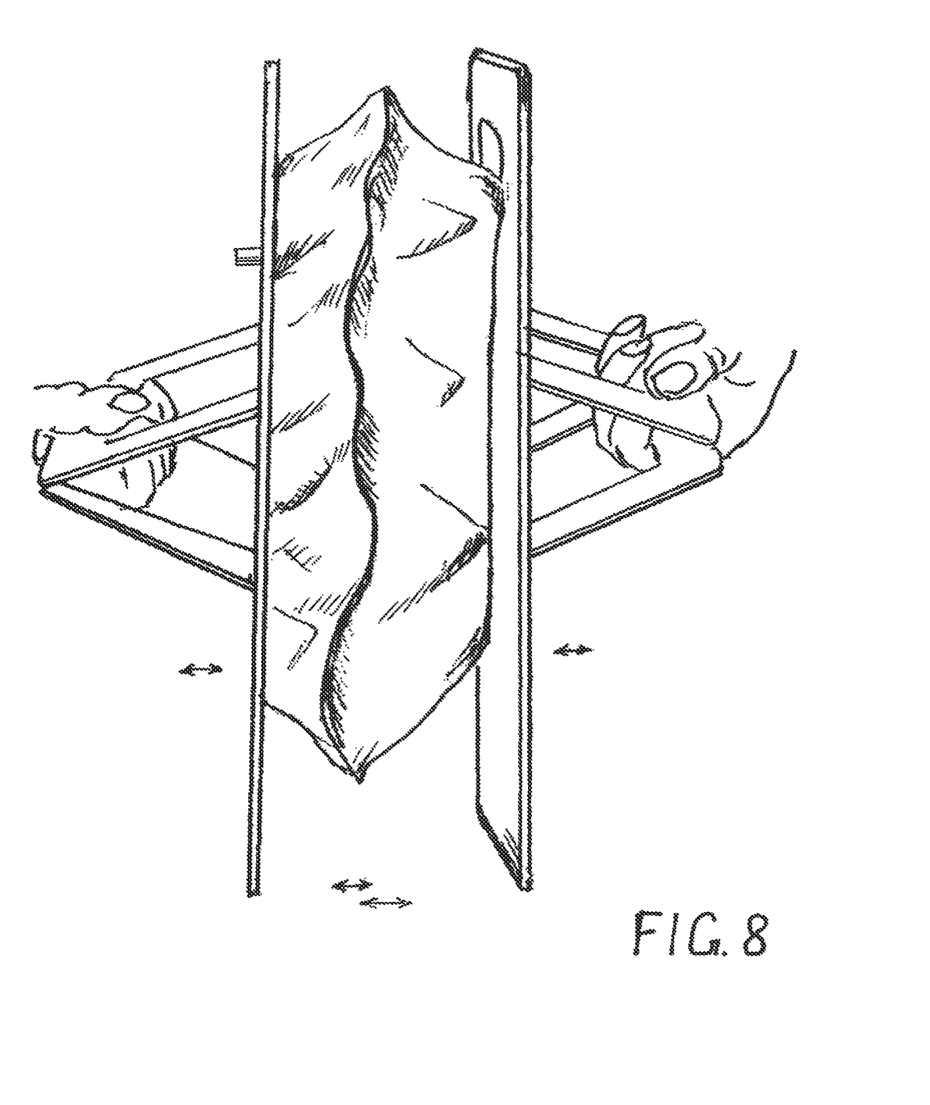

The first method comprises delivering the fluid or fluid sample, e.g. industrial ambient air, into the bag with an external pump. A schematic of this method is depicted in FIG. 8. The sampling method includes a bag 40, a pump 50 powered by a battery 52, and tubing 44 connecting pump 50 to bag 40. Typical personal sampling pumps are suitable for this sampling method.

Bags may be used for preparing standard fluid mixtures or for sampling. When preparing standard fluid mixtures, first the bag is filled with an appropriate measured volume of carrier fluid. The clean carrier gas is dosed with a quantity of fluid, typically, added by pump or syringe as shown in FIG. 8. When used for sampling, a sample of an environment is delivered through the pump and tubing into the bag. The bag is then sealed and sent to a laboratory for analysis.

There are advantages and disadvantages to using this method with sampling bags. The disadvantages include the cost, inaccuracy, and potential contamination from using an external pump to deliver and withdraw the fluid mix. The contamination or inaccuracy can occur from sorption and desorption of some chemicals or components of gas mixture or sample on the walls of the tubes, internal part of the pumps, filters, tubing and connectors. The same problem is caused by sorption of chemical components on the walls of the sampling bag. Even with cleaned walls, active adsorbing sites on the walls can reduce the concentration of certain chemicals when the sample gas is subsequently removed and analyzed. This adsorption may decrease the recovery of certain chemical compounds up to 15%. The recovery rates of this method can be improved with the use of expensive stationary pumps and connection tubes, especially for sampling of trace components.

These methods may also be improved by using a different configuration of pump and the sampling bag. In this configuration shown in FIG. 10, the flexible sampling bag 40 is hermetically sealed within an outer container 60 with rigid walls. The air from the outer container is evacuated through tubing 44 by a pump 50. The pump may be powered by battery 52. As the pressure in the outer container 60 is reduced and bag 40 expands and air from the surrounding environment enters the bag 40. Thus the vacuum outside of the bag 40 and within the container 60 is a driving force for fluid sampling. In the embodiment shown in FIG. 10, the inlet of a sampling bag is connected directly with the ambient fluid. This method does not suffer from one of the major drawbacks of the configuration shown in FIG. 10. The sample taken in the configuration of FIG. 10 does not contact the pump 50 or tubing 44, therefore, there is no sorption or cross-contamination from the walls of the tubing 44, connectors, filter or parts of the sampling pump 50. The other drawbacks of the configuration of FIG. 8 are, however, still persisting in the alternative configuration of FIG. 10, for example, the components is bulky and heavy; the equipment is expensive; the pump requires a battery and frequent maintenance; the sorption on the walls of the bag is the same as described above.

Various embodiments of these methods are described United States patents. For example, U.S. Pat. No. 3,866,474 to Hasselman describes a system in which a sample and an inert gas are drawn into a sample bag within a hermetically sealed container. U.S. Pat. No. 3,965,946 to D'Alo describes improvements in the construction of the outer container. U.S. Pat. No. 5,437,201 to Krueger describes a method of repeatedly purging the sampling bag within the outer container. More sophisticated devices are disclosed in U.S. Pat. No. 5,714,696 to Yemans. The devices attempt to overcome the disadvantages of the system to obtain samples with very low contamination levels. U.S. Pat. No. 6,338,282 to Gilbert describes an apparatus for collection of liquids proves the versatility of this approach. More recently U.S. Pat. No. 6,993,985 to Srebro describes using the apparatus combined in single device yet connected to external vacuum source. Despite of cleanliness suggested by this method, it is using comparably heavy, bulky and expensive equipment requiring calibration and battery maintenance.

An attempt to avoid using pumps in the sampling process is disclosed in U.S. Pat. No. 4,546,659 to Gill et al. This patent discloses a small (10 ml) envelope for the collection of atmospheric air samples for subsequent analysis. The envelope is formed of first and second opposed panels of flexible, gas impermeable material which are peripherally sealed to define a collection chamber. The envelope contains expandable means such as a spiral spring or foam. The expandable means transfer force to the walls via guard plate and large septum. These envelopes have several disadvantages. For example, the expandable means in contact with the sampled fluid increases the potential for adsorption by the inner elements, i.e. the spring or, especially, any foam. Further, the expandable means prevents full evacuation of the contents of the envelope. This large surface area for absorption allows only high concentrations of chemical compounds to be sampled with acceptable recovery and accuracy. Further, the envelope cannot be reused, because the sampling volume would need to be purged several times to clean the envelope, however, the self sealing septum of the envelope does not allow such a procedure.

Accordingly, there is a need for a device that allows use of sampling bags without external hand or electric pumps and without connecting tubes. There is also a need for a device capable of fast grab sampling and fast consecutive strokes/flushes of the sampling bag, thereby to allow sorption equilibrium on the bag's walls. There is a further need for a device that simplifies sampling such that personnel with minimal training may properly use and perform industrial hygiene sampling. There is a further need for such a device that is inexpensive, easy to manufacture, designed for multiple use, may be used with both sampling bags specially designed and conventional sampling bags, light, not bulky, hand or self operated and easy to transport, and/or intrinsically safe in use.

SUMMARY OF THE INVENTION

Embodiments of the present invention are directed to a device for filling and emptying sampling bags. Embodiments of the device comprise mechanical means to expand the sampling bag thereby creating a reduced pressure inside the sampling bag relative to the environment to be sampled. The expansion of the sampling bag creates the driving force for a fluid to be sampled to fill the bag. Embodiments of the device may utilize conventional sampling bags or sampling bags specially designed for embodiments of the device.

Embodiments of the device allowing relatively fast grab sampling and convenient flushing for achieving on-the-wall equilibrium of the sampled air contaminant. Further embodiments of the device may be used with sampling bags for a sampling system which permits sampling without any additional devices such as pumps and tubing. Additional embodiments of the device comprise flaps capable of being folded to form a box for storage, shipping and/or transportation of the sampled bag. Further embodiments of the device may be used for self sampling.

According to the present invention an embodiment of the sampling device is intended for the same uses as conventional market available sampling bags. Embodiments of the device comprise two surfaces. Each surface of the device may be attached to opposite sides of a sampling bag. In one embodiment, the sampling device comprises substantially rectangular hinged panels, wherein each panel has an inner surface capable of adhering, attaching or otherwise connecting to one side of sampling bag's outer surface. In some embodiments, the inner surface of the panel is removably adhered to the walls of the sampling bag, however, in certain other embodiments the sampling device may be integral or incorporated directly into the sampling bag.

The two opposite side walls of the sampling bag are temporarily engaged with means of engagement mounted on the panels of the clamp. When the clamps are closed, the bag is squeezed substantially to zero volume and, when the clamps are opened, the walls are pulled apart creating a moderate underpressure or a vacuum within the sampling bag. If the sampling bag is opened to the atmosphere, the expansion of the sampling bag allows air to be drawn into the inner space of the sample bag. In any embodiment, the panels may have handles; for convenience.

In another embodiment, the sampling device comprises two panels, wherein the inner surfaces of the panels are hinged such that the inner surfaces are substantially parallel or close to parallel during the sampling. A parallel relationship will allow maximum expansion of a typical conventional sampling bag, however, embodiments of the sampling device may comprise panels with inner surfaces that are not parallel during sampling or embodiments of the sampling device may comprise panels that are only parallel when the device is in the closed position to facilitate evacuation of the sample bag.

The walls of the sampling bag may be sufficiently adhered, attached, or otherwise connected to the panels of the sampling device such that biasing the panels away from each other causes the sampling bag to inflate during the sampling process. In embodiments of the sampling device in which the surface of the panel is temporarily or removable adhered to the wall of the sampling bag, the adhering forces between the panels and bag's walls should to be stronger than the opposing force that are created by the reduction of pressure with the sampling bag. The reduction in pressure will depend upon various forces including, but not limited to, the size of the inlet, the density of the fluid, the force applied to the panels, for example. In embodiments of the sampling device designed for use by hand, the operator can control the pulling forces and/or speed on the clamp panels in order to perform sampling and keeping the bag walls attached to the clamp panels during sampling. For example, the adhering forces between the panels and bag's walls may be provided by one of the following means:

Temporary adhesives, for example, at least a portion of the each of the panels may be temporarily adhered to part of opposite walls of the sampling bag;
Vacuum suction cups situated on the inner surfaces of the panels;
Hook and loop connecters, wherein one part or either the hook or loop is attached on the inner surface of the panels and opposite part is adhered to the bag's walls;
Temporary or permanent adhesive sprays;
Water soluble adhesives such as, but not limited to, thermoplastic water soluble adhesives;
mechanical connectors;
Pressure sensitive adhesives; and
Magnetic materials (for example, magnetic foils) on both contacting surfaces, on the panels and on the bag's surfaces. Magnetic foils may be permanently or temporarily adhered to panel's surfaces and to the walls of the flexible sampling bags, for example, by double adhesive permanently (on specially designed bags) or immediately before use (with typically available sampling bags, for example.).

Any means for adhering, attaching or otherwise connecting the sampling bag to the surface of the panel should be sufficient to keep the bag's walls attached to create a reasonable motive force to drive air into the bag when the panels are moved away from each other. In certain embodiments, the sampling device may comprise substantially rigid panels. As used herein, "substantially rigid" means that the panels may be pulled apart to without sufficient deflation to inflate a sampling bag and pushed together to substantially empty the sampling bag.

Another embodiment of the sampling device comprises a sampling bag with at least one slot or channel incorporated into or on the flexible walls of the sampling bag for mechanically attaching the sampling device to the sampling bag. The sampling device may comprise at least one tab or tine for inserting into the slot or channel of the sampling bag. In other embodiments, the sampling device may comprise adhesive patches or labels that comprise at least one slot or channel. The adhesive patch or label may then be attached to a sampling bag thus providing at least one slot or channel on the sampling bag for connecting to the sampling device. For example, the patch or label may comprise a corrugated portion a patch or label may then be adhered on each side of the sampling bag. In this embodiment, the corrugated portion defines channels and the sampling device may comprise a series of tines with similar pitch or spacing between teeth to correspond with the corrugation. Before use of the sampling bag, the teeth of the fork may engage the corrugated patches or label and transfer pulling or inflating forces to the bag's walls when panels are biased apart.

Embodiments of the sampling device may also be configured as a self sampling device. Embodiments of the self-sampling device comprise means for biasing the walls of sampling bag. For example, an embodiment of the self sampling device may comprise two rectangular panels with accurate shape. In this embodiment, the panels when placed adjacent to each other may substantially resemble the wall of a cylinder. The two panels may be in any shape that may be pushed together to be in a substantially parallel position, then the means for biasing may open and inflate the sampling bag. In certain embodiments, the panels of the self sampling device comprise a material with shape memory to bias the sampling bag walls apart. In other embodiments the self sampling device may comprise flat panels and a spring, coil spring, leaf spring, pneumatic cylinders, or other biasing means for exerting springing forces to bias the panels away from each other.

In the embodiments of the panels comprising a material with a shape memory, the sampling device may comprise two panels in hinged connection on one end. The other end of the panels may be hinged, not hinged, connected or may be unconnected. A cross-section of such an embodiment may resemble a substantially circular or oval shape or semi circular or semi oval shape. In some embodiments, at least a central portion of the panels has a means for temporary engagement of the bag's side walls. When a force is applied, the two panels are pressed close to each other toward a substantially flat shape. After removing the force, the biasing means, elastic forces or shape memory of the panels tend to return the panels to their original cross-sectional shape. Once the walls of the sampling bag are pressed together by a biasing force on to the panels, the panels will then bias the bag's walls apart creating moderate underpressure and, thereby, creating sufficient driving force for fluid to enter the bag.

In certain embodiments of the self sampling device, the surface area of the panels when pressed together is sufficiently larger than the outer surface area of the sampling bag. Further, one end of the panels may be made detachably hinged to the other panel allowing the bag to be removed after being loaded with sampled fluid.

Another embodiment of the self-sampling device may comprise spring biased panels that may be are connected on one side with a hinge and the other side capable of being separated by a biasing force, such as by a biasing means, as described, or by hand. As such, devices may comprise two panels having two opposite sides connected by hinges or a combination such one side comprising a hinge and the other side comprising a spring, or both sides comprising a spring.

An embodiment of the sampling device comprising hinged panels, an inlet port and a biasing means for self sampling may be further envisioned as long term sampling system. For long term sampling the inlet port may be designed or have connected to the inlet port a controllable aerodynamic resistance tube or restriction. For such a design the maximum flow rate drawn into the bag may be a controlled and a reliable, substantially repeatable volume may be drawn over a sampling period to provide reproducible sampling.

Another embodiment of the sampling device comprises a sampling bag having permanently mounted panels of a semi-rigid material on both sides. In a typical embodiment, the shape of the panels is substantially rectangular (though the panels may be any shape) and their size may slightly bigger than the size of flattened bag (though the panels may be any size that is capable of inflating and substantially deflating the sample bag).

In a specific embodiment, at least a central portion of each of the panels is permanently adhered to the flexible sampling bag's sides with an appropriate adhesive. The size of the adhered spot may be approximately ⅓ of the surface area one bag wall but may vary as desired. The panels may comprise means for biasing the panels away from each other, handles of soft material and/or may have precut foldable and retractable handles. The panels may further comprise foldable extensions capable of forming a box construction. The extensions may be folded to form a box to allow convenient storage, transportation and/or mailing of the bag. The extensions may carry strips of adhesive material construction capable of stabilizing the box.

Other aspects and features of embodiments of the device for fluid handling will become apparent to those of ordinary skill in the art, upon reviewing the following description of specific, exemplary embodiments of the present invention in concert with the figures. While features may be discussed relative to certain embodiments and figures, all embodiments can include one or more of the features discussed herein. While one or more particular embodiments may be discussed herein as having certain advantageous features, each of such features may also be integrated into various other of the embodiments of the invention (except to the extent that such integration is incompatible with other features thereof) discussed herein. In similar fashion, while exemplary embodiments may be discussed below as system or method embodiments it is to be understood that such exemplary embodiments can be implemented in various systems and methods. Further, U.S. patent application entitled "CONTAINERS FOR FLUIDS WITH COMPOSITE AGILE WALLS" filed on Feb. 16, 2011 in the name of the same inventors is hereby incorporated by reference in its entirety.

BRIEF DESCRIPTION OF THE DRAWINGS

FIG. 1 Simple two part clamp with sticking means on the inner surface in three positions: 1-A flat bag-start; 1-B partially loaded; 1-C completely loaded bag FIG. 2 Clamp with additional plate, tending to keep the opposite walls of the sampling bag parallel to each other partially loaded FIG. 3 Self opening cylindrical clamp attached to the sampling bag: 3-A side view; 3-B perspective view FIG. 4 Air sampling bags with approximately same internal sampling volume 4-A filed by pressure via pump; 4-B air sampling bag with side plates loaded by stretching the side walls with means attached to them—handles or stretching clamps engaging corrugated material FIG. 5 Device upon invention with side assembled panels: 5-A device upon invention—sampling bag with mounted on both sides rigid flexible surfaces and foldable handles; 5-B device and the way to engage both handles from each side by hand FIG. 6 Process of sampling by mowing away the side surfaces: 6-A start pooling—the inlet is open and air is sucked in; 6-B the bag is completely loaded and the inlet have to be closed FIG. 7 Loading the sampling bag with closed handles: 7-A handles are receded in and inlet is closed; 7-B two opposite edges of the flexible bag's sides are pressed to be taped for mailing or storing FIG. 8 Process of grab sampling—several strokes of loading and emptying the sampling bag to purge it completely before final sampling stroke FIG. 9 Sampling bag with two extended and foldable surfaces capable of forming a box for mailing after sampling FIG. 10 State of the art sampling schematics: 10-A sampling pump filing a sampling bag; 10-B sampling pump puling air from hermetic box containing sampling bag.

DETAILED DESCRIPTION OF THE INVENTION

Embodiments of the sampling device comprise two panels capable of assisting with inflating and deflating the sampling or other bag. One embodiment of the sampling device is shown on FIG. 1, the sampling device 10 comprises an top panel 11 and a bottom panel 13. In this embodiment, the top panel 11 and bottom panel 13 have a substantially rectangular shape and area sufficient to cover a substantial portion of the surface of the sampling bag 40. The top panel 11 and bottom panel 13 have one of their ends rotatably attached with a hinged connection 16. The other ends of the top panel 11 and bottom panel 13 are shaped as handles 19 for easy operation by hands. Other embodiments of the sampling device may comprise panels having other handle designs. The inner surface of the rotatably connected top panel 11 and bottom panel 13 at least partially comprises an adhering means 30 capable of at least temporary adhesion to one surface of the sampling bag 40. The material for adhering means 30 may be selected from one of the group including, but not limited to; a permanent adhesive, a temporary adhesive, a multitude of mini vacuuming cups suction capable do adhering to material with smooth surface such as sampling bag 40 wall surface and attached to the panels; a flat magnetic material mounted on top panel 11 and bottom panel 13 and on both side walls of the sampling bag 40, as well as other adhesives or connectors or combinations of such adhesives and connectors. The shape and the size of panels of embodiments of the sampling device may be any shapes and/or sizes desirable to match or conform to the shape and size of a sampling bag. For example, the surface area of the panels 11 and 13 may be slightly larger than the surface area of the sampling bag. The panel may or many not correspond with the contour of the sampling bias bag, nevertheless a panel with a smaller surface than the sampling bag may also be used, for example, the panels may be smaller if the bag is previously flattened by vacuuming or folding the sampling bag or if the sampling bag has sufficiently stiff or rigid walls. As used herein, the volume of a fully or substantially deflated sampling bag is less than 5% of the fully inflated volume. This remaining volume is substantially negligible once the bag is clean, sufficiently purged, or pre-cleaned before use (as in standard sampling procedure for reuse of sampling bags).

Figure 1:
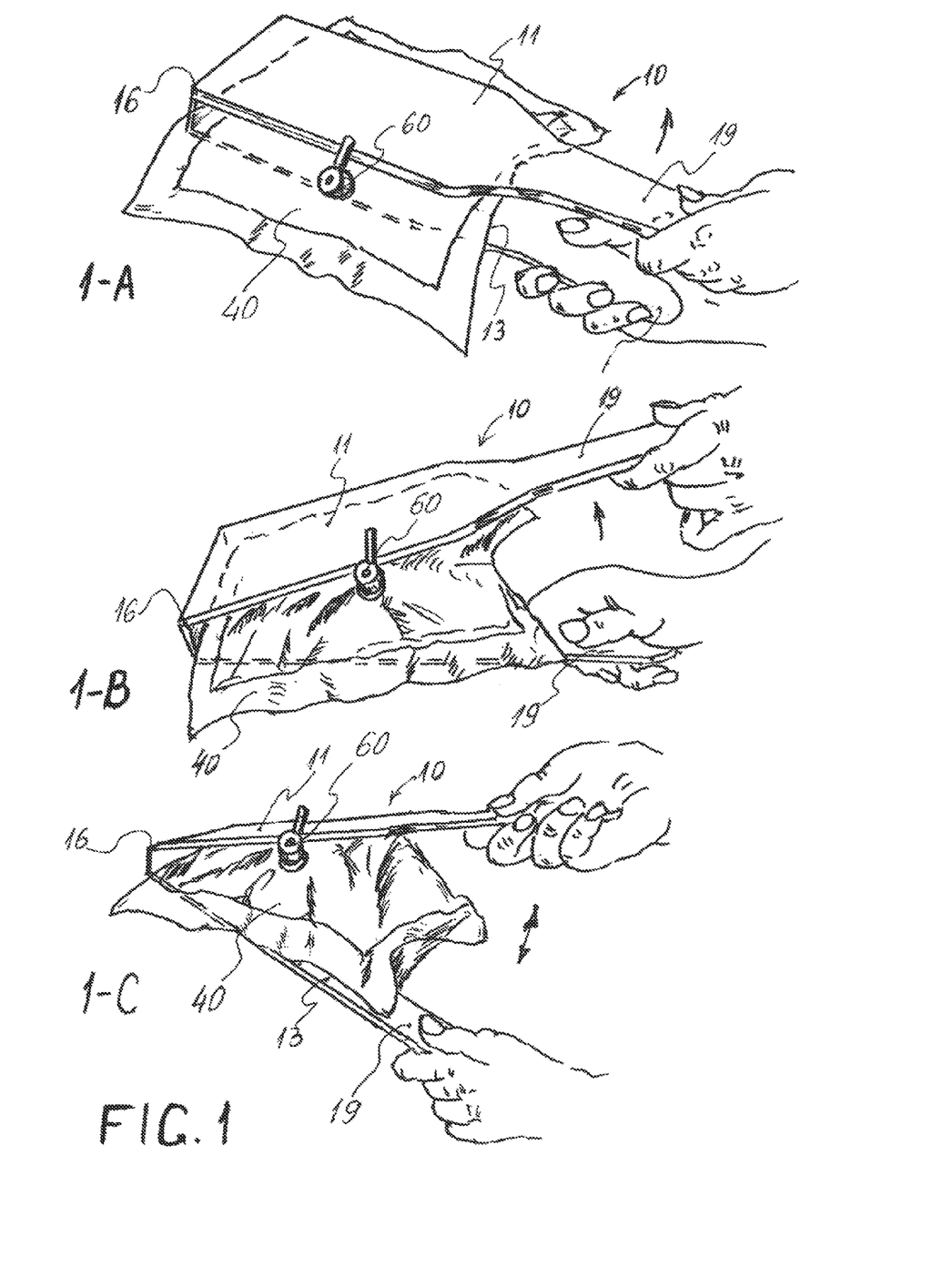

The positioning of the adhering means in the embodiment of FIG. 1 is a contacting line. The adhering means of this embodiment takes much less area of the panels compared to the total panel surface and the sampling bag surface because in the inflated/loaded position the contact area between the bag 40 and the top panel 11 and bottom panel 13 is smaller than in the flattened position. In a general case, this area may be in the range of approximately ⅓ from the total area of the side wall of the flattened sampling bag 40, for example.

Figure 2:
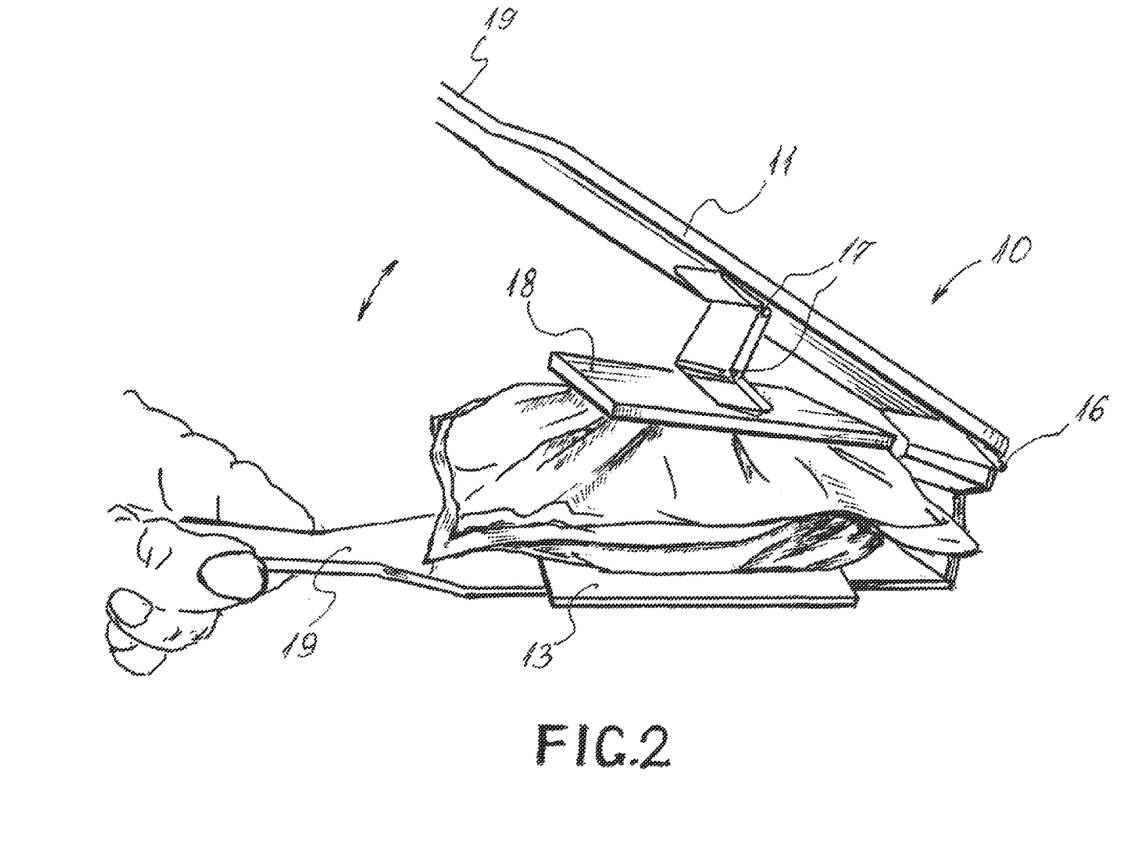

In FIG. 2, a further embodiment of the sampling device is shown. Sampling device 10 Of FIG. 2 comprises an additional connecting plate 18 with a hinged connection 17 to the top panel 11 in order to stay somewhat parallel to the bottom panel 13. For certain shaped bags, a sampling device with a hinged connection 17 may result in more complete loading and/or unloading of the sampling bag 40. The contacting surfaces on the top additional plate 18 as well as bottom panel 13 comprise an adhering means. The embodiments of the sampling device shown in FIGS. 1 and 2 may be used with conventional or standard sampling bags or specially designed sampling bags.

Embodiments of the sampling device may comprise removable and/or changeable panels or a set of removable and/or changeable panels. The panels in the set may be of different size, shape, or include a different adhesive. For example, an embodiment may include a kit of multiple sized panels so the panel may be changed to be more compatible with the size of the desired sampling bag. For example, a smaller panel may be removed and replaced with a panel comprising a larger surface area than the surface area of the sampling bags flexible wall. The embodiments of the sampling devices shown on FIGS. 1 and 2 may be moved away from each other not only by the hands of operator but by other biasing means such as, (but not limited to weights, springs, an electric motor, or other biasing mechanisms as described).

Figure 3:
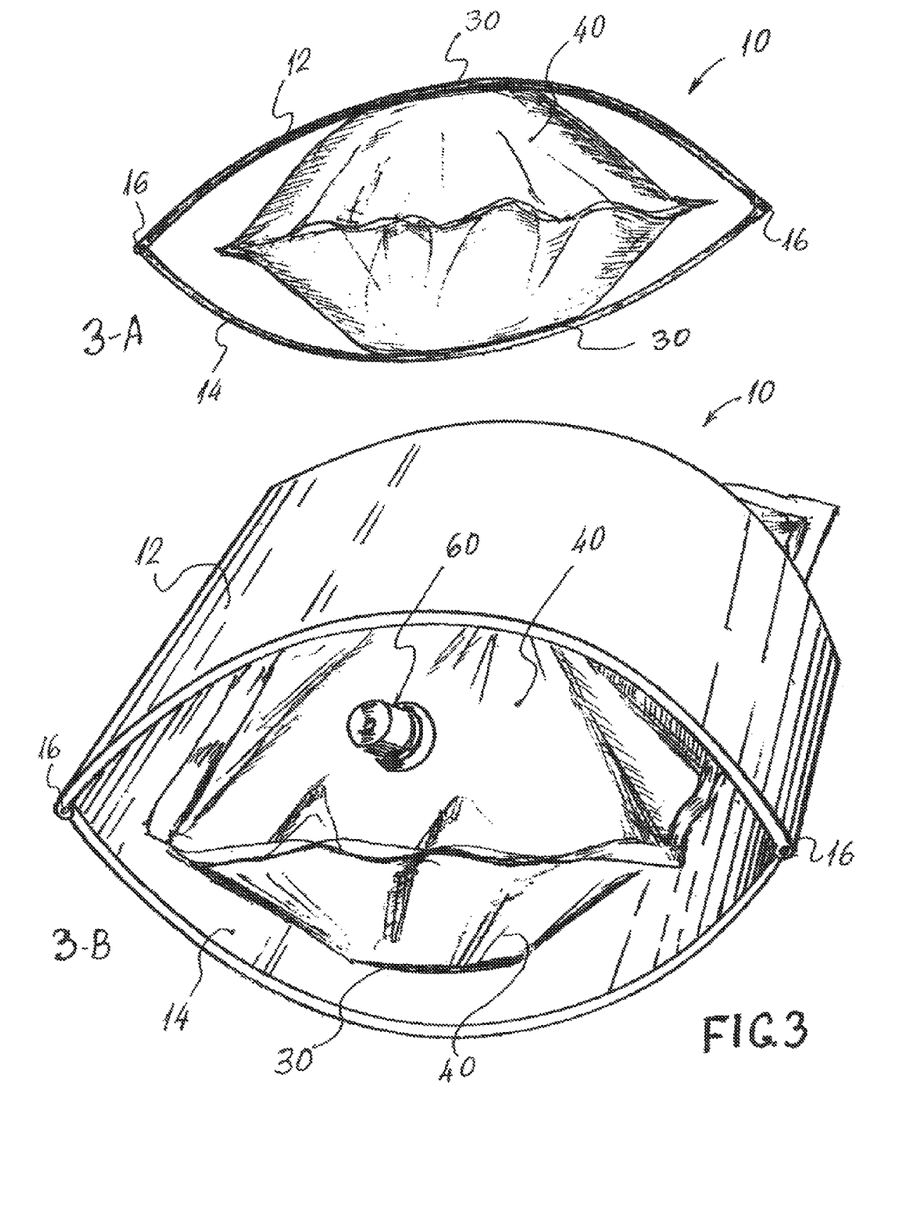

In FIG. 3, another embodiment of the sampling device is shown. The sampling device 10 of FIG. 3 comprises two panels—top panel 12 and bottom panel 14 made from a flexible material with shape memory. Embodiments of the invention may have a cross-sectional shape in the general shape of a cylinder, oval, a portion of a circle, or a portion of an oval. The flexible material for those panels may be selected from a group including, but not limited to plastics, polycarbonates, nylon, polyester, multilayer composite plastics, metals, aluminum, stainless steel alloys, steel alloys, brass and bronze alloys. The top panel 12 and bottom panel 14 may have one or two sides pivotally connected. Certain embodiments of the sampling device comprise a panel having one end pivotally connected to the panel and the other end of the panel comprising a releasably hinged connection. For example, the releasable hinged connection may comprise a pin that may be inserted to make the hinged connection and removed to release the hinged connection. In other embodiments, both ends of top panel 12 and bottom panel 14 may be unconnected or comprise a hinged releasable connection. Each top panel 12 and bottom 14 may be connected to the sample bag as the already discussed with embodiments shown in FIGS. 1 and 2.

The sampling bag 40 of FIG. 3 may be flattened in the cavity formed between top panel 12 and bottom panel 14 when the panels are forced by hands or other biasing force to be substantially flat. In some embodiments, the force may be used to simultaneously connect the sampling bag to the top panel 12 and/or the bottom panel 14 adhering means 30 and compress, deflate or flatten the sampling bag. To perform sampling, the inlet cap or sampling valve 60, FIG. 3-B, is opened and the external force is removed. At that point, the elastic, or shape memory, or other biasing forces on the panels pull the sampling bag walls into an inflated or open position. These biasing forces create initially a small space with underpressure. This underpressure relative to the environment is the driving force for the fluid to pass through the inlet or valve 60 and begin to inflate the bag. The top panel and bottom panels continue to move apart and then stops as the bag is filled. The volume of the sampling bag may be limited by a mechanical stop such as a plastic strip or similar stop, the fully separated position of the shape memory panels 12 and 14, the length or shape of the biasing means, or other mechanical limitation of the sampling bag or sampling device. The device thus provides a self sampling device that may be filled over an extended period or cycle and the sampling time for this cycle is limited mainly by the biasing forces and the aerodynamic resistance and/or flow of fluid through the inlet port or valve 60. As the valve may switched between different aerodynamic resistances, the sampling time may varied between short sampling periods to long sampling periods. The sampling time may be controlled by the biasing means of the panels and/or the sampling inlet or design of valve to vary from very short time, (grab sample) to 15, 30 min, 1 hour, 8 hours, or days, or other desired sample time.

Figure 10:
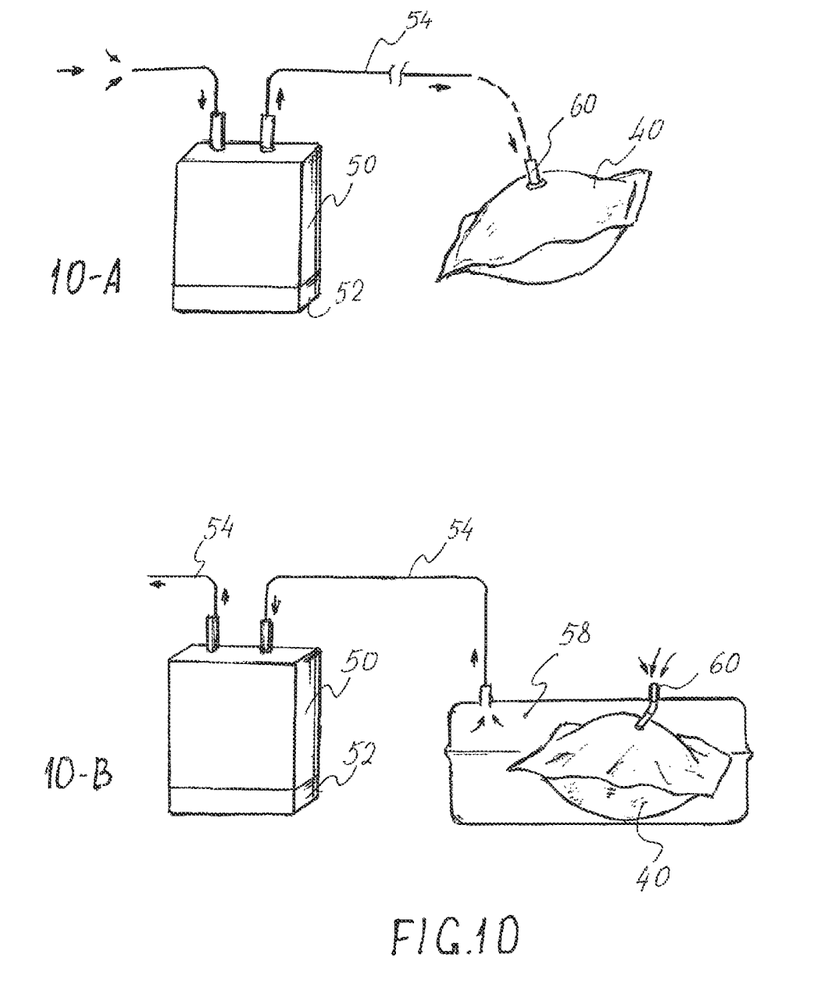

Compared to the prior art systems used to fill the bag for short sampling or for extended period sampling shown in FIG. 10, the devices upon present invention are much lighter, simpler and less expensive.

Figure 4:
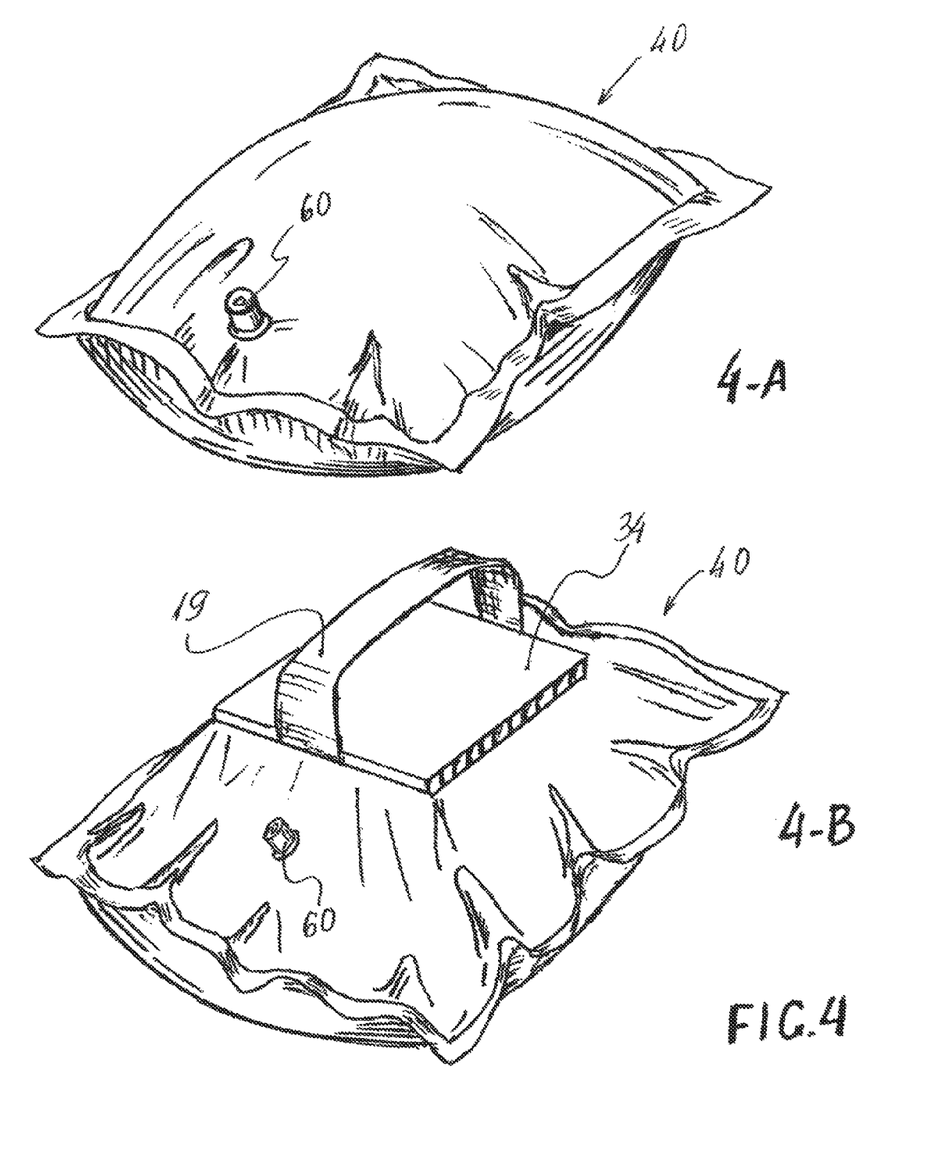

A still further embodiment of the sampling device is shown in FIG. 4-B. This embodiment of the sampling device 40 comprises a top panel 34 that has a surface area that is smaller than the surface area of the wall of the sampling bag. In some embodiments the sampling device may have a panel 34 that is merely sufficient for attaching handle 19 to the sampling bag 40. In other embodiments, the handle 19 may be directly attached to the sampling bag. In this design, the bags may be deflated by connecting inlet 60 to a vacuum source, for example. The bag may then be conveniently stored in a deflated state until needed. The sampling device may then be used to obtain a sample by simply opening inlet 60 and pulling the handle 19 or handles 19, if applicable. Such an embodiment gives the sampling bag unique properties to be stored in small space and when needed for sampling purposes may be easily used without any other apparatus and complicated system with tubing, etc.

Figure 5:
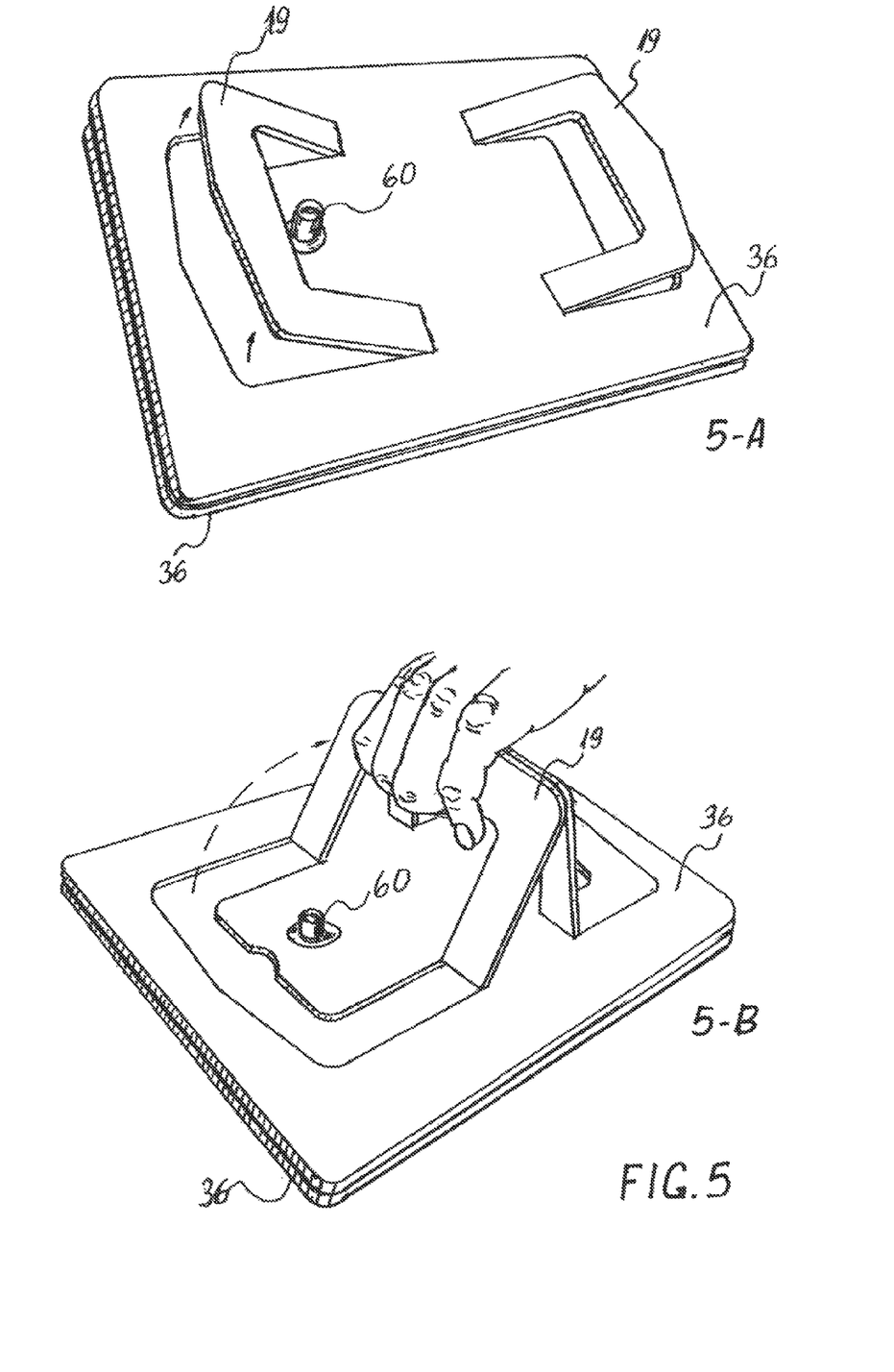
Figure 6:
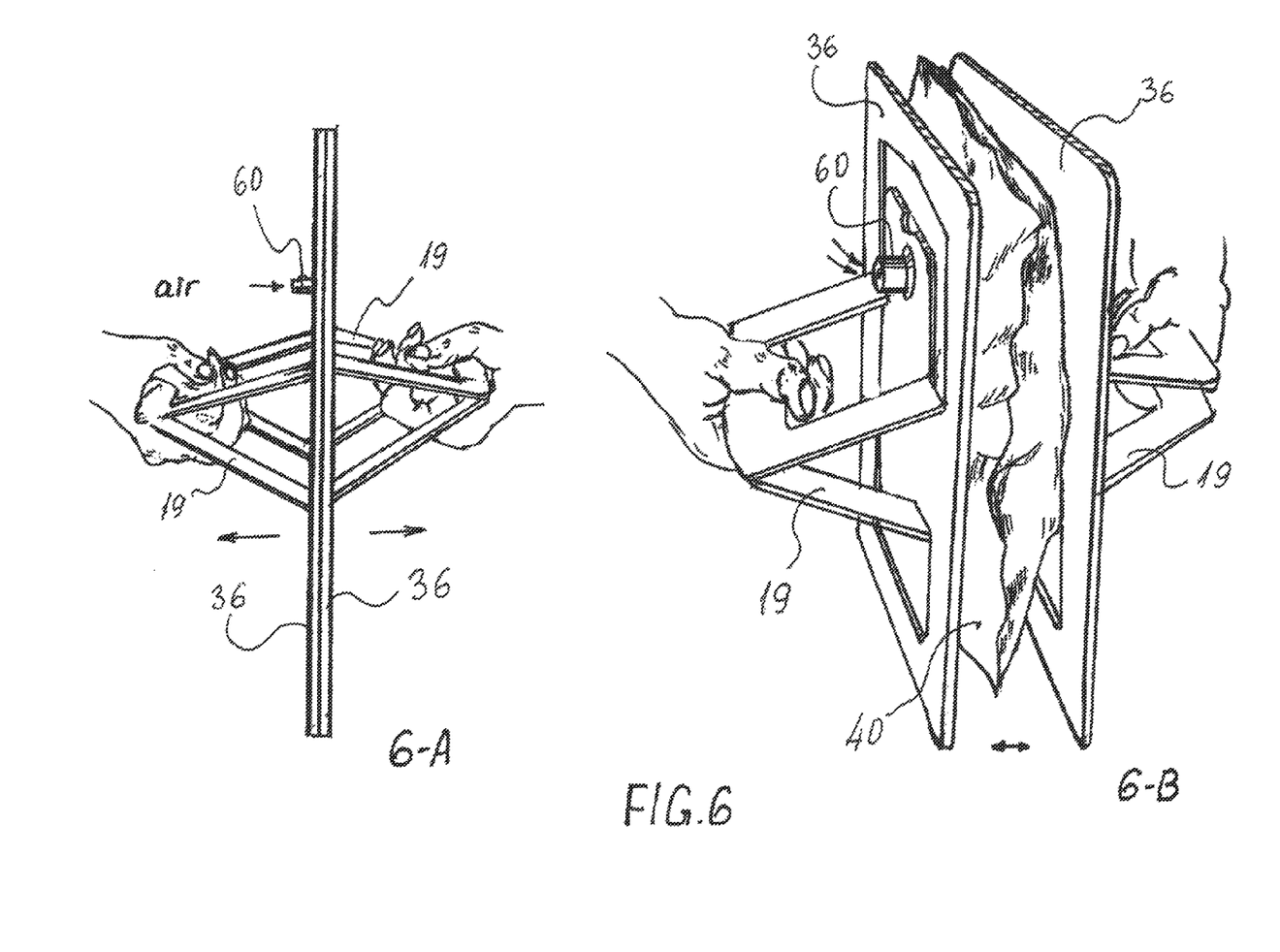
Figure 7:
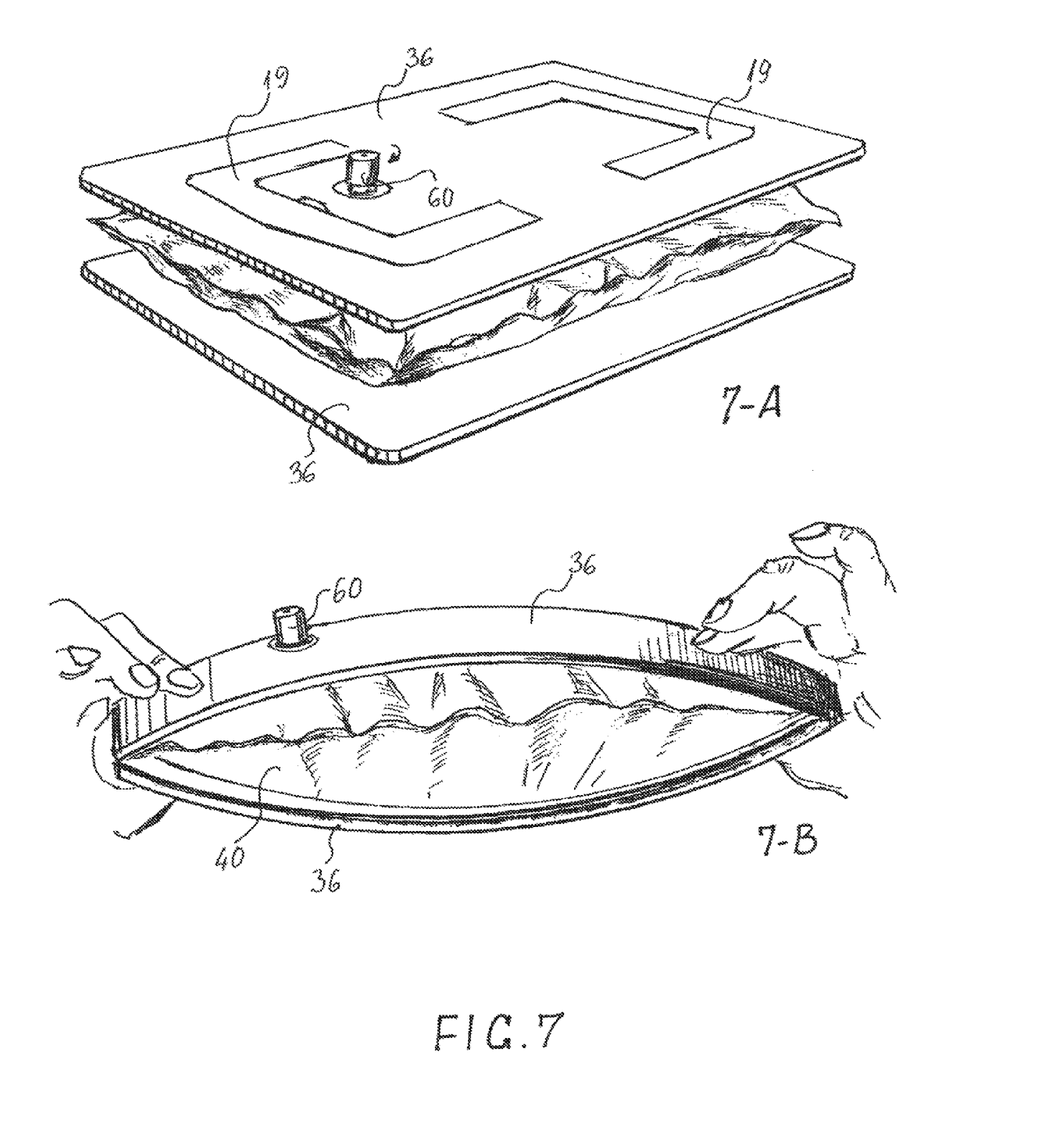

In certain embodiments of the sampling device, the panels 34 may be made from corrugated material having inside channels which may be engaged by fork-like means as discussed per FIGS. 1 and 2. A still further embodiment of the sampling device is shown in FIGS. 5A and 5B. The sampling bag may be flattened between the two panels 36 as shown on FIG. 5-A. In the panels 36 foldable handles are precut and can be easily moved up as shown on FIG. 5-A and then engaged by hands as shown in FIG. 5-B. For grab sampling the inlet 60 may be completely opened and sampling bag 40 can be filled by pulling handles 19 until the bag is appropriately filled with the targeted fluid as shown on FIGS. 6-6-A and 6-B. Then the handles 19 may be folded flat as shown on FIG. 7-A and both sides can be pushed towards each other shown on FIG. 7-B and edges fixed with tape, clips or other means to ease insertion in an envelope for storage or shipping. Embodiments of the sampling bag may include such panels incorporated directly into the walls of the sampling bag.

For grab sampling, as previously mentioned, the bag may be flushed several times in by inflating and deflating the sampling bag as shown on FIG. 8 until the inside volume is purged and the inside walls are substantially at equilibrium with the targeted substances in the sampled fluid. This will gives the sampling device the unique feature of achieving almost 100% recovery, compare to 85-90% with one only sampling suction from prior art devices.

Figure 9:
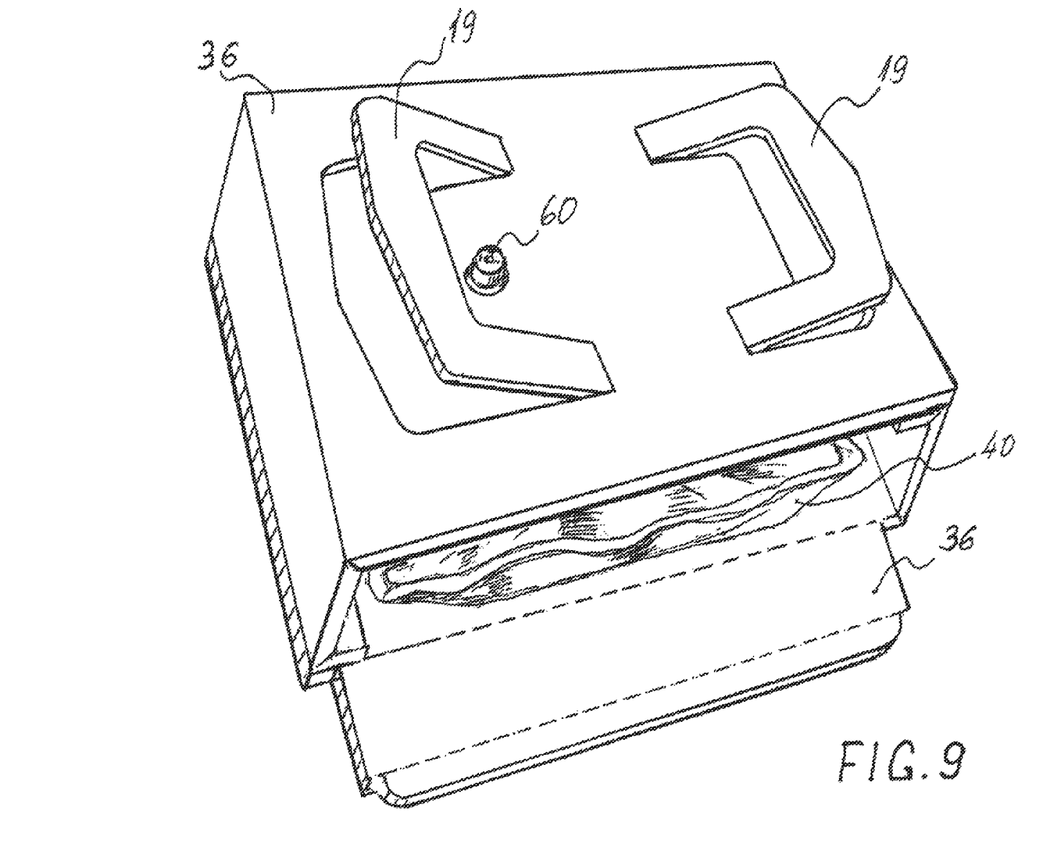

Another embodiment is depicted in FIG. 9 demonstrates the versatility of the concept allowing the extensions of side panels 36 to be used after sampling to form a rigid wall box convenient for prolonged storage or mailing of the sample.

Embodiments of the devices upon present invention have many unique features as compared to conventional sampling bags and methods, embodiments of the sampling bag have some or all of the following features:

No pumps of any type are required to expel or to fill fluids into sampling bags;
No battery charging and maintenance;
No pump calibration;
Extreme simplicity of operation—no requirement of special instruction or qualification;
Inexpensive sampling process;
Low cost of manufacturing;
Higher recovery when sampling, close to 100%;
Substantially no sorption on the walls of external lines or inside pumps;
Substantially no cross-contamination;
Substantially all of the sampled volume is usable;
Convenient for sampling;
Allows self sampling for extended sampling times;

Easily portable sampling system;

Even loaded the sampling devices are portable and easy to mail; and

The devices are intrinsically safe and provide intrinsically safe sampling.

The embodiments of the described methods and device for fluid sampling are not limited to the particular embodiments, method steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The invention claimed is:

1. A sampling device, comprising:
    a sampling bag for sampling fluids comprising at least two flexible walls defining an internal sampling volume and an inlet port defined by one of the two flexible walls providing communication between an ambient fluid to be sampled and the internal sampling volume;
    a top substantially rigid panel connected to one of the flexible walls on a first side of the sampling bag;
    a bottom substantially rigid panel connected to the other of the flexible walls on a side opposite of the first side of the sampling bag; and
    biasing means for exerting springing forces on the panels to bias the panels away from each other.

2. The sampling device of claim 1, wherein biasing means is one of a spring, a coil spring, a leaf spring, and a pneumatic cylinder.

3. The sampling device of claim 1, wherein the top substantially rigid panel and the bottom substantially rigid panel are rotatably attached with a hinged arrangement at one end.

4. The sampling device of any of claim 2, wherein the two panels are releasable connected to the flexible walls of a sampling bag such that the sampling bag is configured to be removed from the top substantially rigid panel and bottom substantially rigid panel without damaging the sampling bag.

5. The sampling device of any of claim 1, wherein the two substantially rigid panels are permanently connected to the flexible walls of a sampling bag.

6. A sampling device, comprising:
    a sampling bag for sampling fluids comprising at least two flexible walls defining an internal sampling volume and an inlet port defined by one of the two flexible walls providing communication between an ambient fluid to be sampled and the internal sampling volume;
    a top substantially rigid panel connected to one of the flexible walls on a first side of the sampling bag;
    a bottom substantially rigid panel connected to the other of the flexible walls on a side opposite of the first side of the sampling bag; and
    wherein the panels comprise flaps, wherein the flaps are configured to be folded to form a box.

7. The sampling device of claim 6, wherein the box is a shipping box.

8. The sampling device of claim 6, wherein the flaps comprise strips of adhesive material configured to stabilize the box.

9. The sampling device of claim 6, wherein the panels comprise Retractable handles.

10. The sampling device of claim 9, wherein the retractable handles are precut and foldable.

* * * * *